United States Patent [19]

Jeanne et al.

[11] Patent Number: 5,109,022
[45] Date of Patent: Apr. 28, 1992

[54] NON-INSECTICIDAL INSECT REPELLENT

[75] Inventors: Robert L. Jeanne, Madison; Gregg Henderson, Cross Plains, both of Wis.

[73] Assignee: Wisconsin Alumni Research Foundation, Madison, Wis.

[21] Appl. No.: 602,835

[22] Filed: Oct. 24, 1990

[51] Int. Cl.$^5$ ............................................. A01N 37/02
[52] U.S. Cl. ................................... 514/552; 514/919; 424/DIG. 10
[58] Field of Search .............................. 514/552, 919; 424/DIG. 10

[56] References Cited

U.S. PATENT DOCUMENTS

| | | | |
|---|---|---|---|
| 4,147,800 | 4/1979 | Singer et al. | 424/312 |
| 4,320,139 | 3/1982 | Takei et al. | 424/282 |
| 4,490,360 | 12/1984 | Antonik | 424/95 |
| 4,707,496 | 11/1987 | Simmons | 514/531 |
| 4,762,716 | 8/1988 | Moeschler et al. | 424/195 |
| 5,006,562 | 4/1991 | Steltenkamp | 514/919 |

OTHER PUBLICATIONS

King, W. V. Chemicals Evaluated as Insecticides and Repellents at Orlando, Fla., U.S. Dept. of Agriculture, 1954, pp. 13-16, 232, 250-251.

R. L. Jeanne (1970), "Chemical Defense of Brood by a Social Wasp," *Science*, 168: 1465-1466.

S. Turilazzi and A. Ugolini (1979), "Rubbing Behavior in Some European *Polistes* (Hymenoptera: Vespidae)," *Psyche*, 87: 49-58.

J. Kojima (1983), "Defense of the Pre-emergence Colony Against Ants by Means of a Chemical Barrier in *Ropalidia fasciata* (Hymenoptera: Vespidae)," *Jpn J. Ecol.*, 33: 213-223.

D. C. Post, et al. (1984), "Identification of Ant Repellent Allomone Produced by Social Wasp *Polistes fuscatus* (Hymenoptera: Vespidae)," *J. Chem. Ecol.*, 10: 1799-1807.

D. C. Post, and R. L. Jeanne (1981), "Colony Defense Against Ants by *Polistes fuscatus* (Hymenoptera: Vespidae) in Wisconsin," *J. Kans. Entomol. Soc.*, 54: 599-615; and Post et at., supra., 1984.

Agriculture Handbook No. 340, Agricultural Research Service, United States Department of Agriculture, 1967.

*Primary Examiner*—Allen J. Robinson
*Assistant Examiner*—John D. Pak
*Attorney, Agent, or Firm*—Andrus, Sceales, Starke & Sawall

[57] ABSTRACT

The present invention describes a composition and method for repelling flying, biting and stinging insects without having insecticidal effects. The method includes the step of applying an insect repelling substance, which includes methyl myristate, methyl palmitate, butyl palmitate or combinations thereof in a selected quantity to a surface.

10 Claims, No Drawings

NON-INSECTICIDAL INSECT REPELLENT

This invention was made with United States government support awarded by USDA, HATCH Funds. The United States Government has certain rights in this invention.

FIELD OF THE INVENTION

The present invention is directed to insect repellents in general, and particularly to an insect repellent for flying, stinging and biting insects. The present invention is specifically directed to the use of methyl myristate, methyl palmitate and butyl palmitate as insect repellents.

DESCRIPTION OF THE PRIOR ART

Control of insects is usually attempted by the use of insecticides or of insect impermeable barriers. Unfortunately, insecticides carry with them the risk of contamination of materials or areas where the presence of an insecticide is not desired. Additionally, insecticides often unintentionally destroy other beneficial species. Insect-proof barriers are not always suitable to the physical situation in which protection from insects is required. Insecticides and insect repellents are of course well-known in the prior art, as is evidenced by the following patents.

U.S. Pat. No. 4,147,800 to Singer, et al. is directed to a pediculicide, specifically for use with lice, comprising an admixture of an aliphatic alcohol and an aliphatic ester.

U.S. Pat. No. 4,490,360 to Antonik is directed to an insect repellent which comprises as an active component a naturally derived composition from fireflies. Although the firefly extract is designed to repel certain insects, no repellent effect is demonstrated against stinging insects.

U.S. Pat. No. 4,707,496 to Simmons is directed to an insect repellent soap composition which includes, as an active ingredient, a repellent chemical such as N,N-diethyl-metatoluamide, and an insecticide such as 3-phenoxybenzyl ($\pm$), cis trans-2,2-dimethyl-3-2(3,3 dichlorvinyl) cyclopropane-1-carboxylate. The soap is designed to have repellent properties against biting insects.

U.S. Pat. No. 4,762,716 to Moeschler, et al. is directed to annonin, a compound having insecticidal properties.

U.S. Pat. No. 4,320,139 to Takei et al. is directed to a method of enhancing the activity of fast-evaporating insecticides by incorporating in the insecticide one or more compounds which is/are designed to enhance the degree of evaporation of the active ingredient. The addition of the compound is alleged to enhance the activity of the insecticide to provide rapid and effective killing of insects.

Various species of insects and other arthropods are also known to produce repellents and other chemical defenses against enemy insects. See, for example, M. S. Blum (1981) *Chemical Defenses of Arthropods*, Academic Press, New York. In the Hymenoptera, a large, highly specialized order of stinging insects such as the bee or wasp, exocrine products ranging from hydrocarbons to acids have defensive functions in such insects as sawflies and ants. Wasps are armed with venom, but in addition female social wasps of the genera Mischocyttarus, Polistes, and Ropalidia are known to rub a secretion onto their nest which repels foraging ants. See: R. L. Jeanne (1970) "Chemical Defense of Brood by a Social Wasp," *Science, b 168, 1465-1466;* S. Turilazzi and A. Ugolini (1979) "Rubbing Behavior in Some European Polistes (Hymenoptera: Vespidae)" *Psyche,* 87, 49-58; and J. Kojima (1983), "Defense of the Pre-emergence Colony Against Ants by Means of a Chemical Barrier in *Ropalidia fasciata* (Hymenoptera: Vespidae)" *Jpn. J. Ecol.* 33, 213-223. However, such wasp glandular secretions contain many different chemicals. As such, it has been difficult to determine which chemicals are effective as a repellent and upon which insects they are effective.

It has recently been discovered that wasps, particularly social wasps of the genus Polistes, produce an ant repellent in order to provide a barricade between a wasp colony and foraging ants. One of the active components in the defensive secretion of *Polistes fuscatus* (F.) is methyl palmitate, $C_{17}H_{34}O_2$ (methyl hexadecanoate) (Post, D. C. et al., 1984, "Identification of Ant Repellent Allomone Produced by Social Wasp *Polistes fuscatus* (Hymenoptera: Vespidae) *J. Chem. Ecol.* 10: 1799-1807). Ants of several species were determined to be reluctant to cross barriers of the natural methyl palmitate repellent, synthetic methyl palmitate, or its methyl ester homolog, methyl myristate (Post, D. C. and R. L. Jeanne, 1981, "Colony Defense Against Ants by *Polistes fuscatus* (Hymenoptera: Vespidae) in Wisconsin," *J. Kans. Entomol. Soc.,* 54: 599-615; and Post et al., supra., 1984).

While the above-mentioned compounds have been found to form an effective repellent for some species of ants, they have not been tested or, alternatively, have not previously been found to provide an effective repellent against flying and stinging insects, and particularly social insects of the flying and stinging varieties. Additionally, there is no presently known compound which provides effective repelling relief against flying, biting and stinging insects without also being an insecticide.

SUMMARY OF THE INVENTION

The present invention is specifically directed to a repellent for a class of insects known as social insects. Social insects are characterized by a number of unique traits. For example, social insects have overlapping generations, i.e., they can build enormous populations. Social insects are characterized for their ability to care for their young. Additionally social insects have a marked caste system including a queen, workers, soldiers, etc.

The insects involved herein include the class Insecta, and particularly flying, stinging and biting insects, including bees, wasps and flies, which are generally pestiferous. More particularly the insects involved here include social insects such as honey bees (*Apis mellifera*), and yellow jackets such as the German yellow jacket (*Vespula germanica*).

The importance of this discovery does not overlook the beneficial aspects of social Hymenoptera. Ants and wasps in particular have been shown to reduce populations of pest species, especially in forest systems. Honey bees are one of the most, if not the most, important pollinators of crops. Without honey bees, millions of dollars in reduced yields would be realized. The repellent of the present invention is beneficial in that it will allow amicable ecosystems of human and insect populations.

The present invention is directed to a method for repelling flying, biting or stinging insects from a surface comprising applying an effective repelling quantity of methyl myristate, methyl palmitate, butyl palmitate or a combination thereof to the surface.

The present invention is also directed to a repellent for flying, biting and stinging insects comprising an effective repelling quantity of a component selected from the group consisting of methyl myristate, methyl palmitate and butyl palmitate, or a combination thereof, and a carrier.

The present invention is further directed to an artificially produced surface having repelling characteristics directed to flying, biting and stinging insects comprising a surface treated with an effective repelling quantity of a component selected from the group consisting of methyl myristate, methyl palmitate and butyl palmitate, or a combination thereof, and a carrier.

A principal advantage of the insect repellent of the present invention is that it is a repellent, and not an insecticide. Thus, the compounds act as repellents against insects, not toxins. Because these repellents can be naturally produced and do not kill the insects, they will not select as easily for resistance in populations of the target insect. Additionally, the repellents have been found to show low mammalian toxicity. For example, butyl palmitate has been used in packaging beer. Further, methyl palmitate is used in many cosmetics and hand lotions.

Another advantage of the present invention is that the compounds are readily available and relatively inexpensive to synthesize.

The repellents of the present invention show promise as useful products to be employed against disease carrying, stinging and/or generally pestiferous insects.

Further objects, features and advantages of the invention will be apparent from the following detailed description of the method and composition of the present invention.

DETAILED DESCRIPTION OF THE INVENTION

The present invention is specifically directed to the use of methyl myristate, methyl palmitate, butyl palmitate and combinations thereof as a repellent for flying, biting and stinging insects, and particularly as a repellent against stinging Hymenoptera, a large, highly specialized order of stinging insects, including bees and wasps.

It had previously been found that a secretion produced by the social wasp *Polistes fuscatus*, referred to above, contains methyl palmitate in a biologically active form. The secretion is generally utilized by the wasp to repel foraging ants from the wasp's nest. Additionally, a methyl ester homolog of methyl palmitate, methyl myristate, exhibits similar repellent activity.

The repelling activity of methyl myristate, methyl palmitate, and butyl palmitate is concentration-dependent, with increasing quantities of the substances generally proving increasingly successful in repelling insects. Methyl myristate, methyl palmitate and butyl palmitate shall sometimes be referred to hereinafter as the "repelling substances" or, with respect to their inclusion in insect-repelling preparations and the like: "active ingredients." These repelling substances are substantially insoluble in water, but are soluble in isopropyl alcohol, ether, hexane, and similar nonpolar solvents. At room temperatures, methyl myristate and butyl palmitate are oily liquids, and methyl palmitate is a solid obtainable commercially as a powder.

A preparation for repelling flying, biting and stinging insects may be made by dissolving or dispersing the repelling substances in a suitable liquid carrier, or mixed or adsorbed with an appropriate solid carrier to process it into a desired form for use as an insect repellent. As preferable forms of preparation, the composition can be prepared as an emulsifiable concentrate, a wettable powder or a liquid. These preparations can be prepared, if desired, by methods known to the art, such as by adding emulsifying agents, suspension agents, spreaders, penetrants, wetting agents, tackifiers and stabilizers. Suitable solid carriers include, without limitation, vermiculite, perlite and charcoal.

The liquid carrier used is preferably a nonpolar solvent having a high vapor pressure at room temperature, so that, once the carrier with dissolved repelling substance is applied to a selected surface, such as a foundation, doorway, packaging material, the skin surface, or the like, the liquid carrier will quickly evaporate without staining, leaving the repelling substance behind, deposited on the surface. Such applications may be made by spraying, painting, dipping, or any conventional method of applying a liquid repellent or the like. A preparation for repelling the insects may also be made by forming a suspension of a repelling substance in a liquid carrier in which it is substantially insoluble.

Alternatively, the repelling substance may be used with a selected extender, such as a solid extender capable of adsorbing a solution of the repelling substance in a liquid carrier. By application of such a solution to the liquid extender, with subsequent evaporation of part or all of the liquid carrier, the extender may be impregnated with the repelling substance. The repellent in the extender may then be employed in areas or applications where use of a liquid is undesirable, for example, or where it is desired not to leave a permanent deposit of the repelling substance on an underlying surface or where for any reason it is undesirable to charge the atmosphere with the evaporating carrier. The solid extender may be finely subdivided. An example of such solid extenders include sawdust, particulate clay, etc. Alternatively, the solid extender may be sheet material such as cardboard or paper, a spun, foamed, or matted material such as insulation for building purposes, or a block such as lumber or paraffin blocks or the like.

A liquid extender is also possible. Thus, a non-polar liquid such as hexane in which an active ingredient is dissolved may be utilized in a suspended form in water, the water serving as the extender. Such suspensions may be made up by an end user just prior to application by a simple process of combining the solution of active ingredient with a quantity of water and shaking. The process is a familiar one to users of water insoluble repellents or insecticides supplied in concentrated, dissolved form.

The proportion of the active ingredients contained in the insect repellent of the present invention is suitably in the range of 1 to 40 volume percent, preferably 3 to 10 volume percent in the case of a liquid carrier; and 1 to 40 volume percent in the case of a solid carrier, preferably from 3 to 10 volume percent.

An alternative carrier can be in the form of an ointment such as, for example, mineral oil, polyethylene glycol, pectin, polyhydric alcohol, liquid paraffin, i.e., paraffin oil, vegetable oils, white oil, lanolin and resins. Paraffin oil serves nicely because it is non-toxic, nonreactive, protects the dispersed repellent molecules from environmental alteration, slows the release of the repellents into the atmosphere and adheres to skin, hair, fur, clothing and most other treatment surfaces. Any carrier meeting these criteria should be considered to fall within the scope of the claims of this invention. The proportion of the ointment base to the active ingredient in the liquid carrier contained in the insect repellent composition of the present invention may range from 60 to 99 volume percent, preferably from 90 to 97 volume percent.

The method of imparting insect-repelling properties to a base substance includes the step of applying an active ingredient including one of the group consisting of methyl myristate, methyl palmitate, butyl palmitate, or a combination thereof, to the surface in insect-repelling quantities. The base substance may be a liquid in which the active ingredient(s) is/are dissolved so that the step of applying an active ingredient includes the step of dissolving it in the liquid. Alternatively, the base substance may be a liquid in which the active ingredient may be suspended by simple mixing, homogenizing, or any of the various well-known and conventional methods for making a suspension.

The base substance may as easily be a solid material that is impregnable by the active ingredient by direct application or otherwise. Thus, the method of the invention may include applying the active ingredient to the solid material dissolved in a selected quantity of a liquid carrier. The solid material may then be dried to remove the liquid carrier and leave an insect-repelling quantity of the active ingredient behind on the solid. Alternatively, a suspension of the active material in a liquid may be used instead of the solution referred to. It is also possible that the base substance may be a solid material with which the active ingredient may be physically intermingled. In that case, the step of applying an active ingredient would include the step of physically intermingling the active ingredient with the solid material, a step that could be undertaken by any conventional means of mixing two solid materials or an oil with a solid material. Melting the active ingredient and solid material together, intermingling particles of the solid material and an active ingredient in solid form, and spraying or otherwise applying the active ingredient in liquid form to particles of the solid material all are examples of the many conventional means of mixing known to those skilled in the art.

The invention further includes insect-repelling preparations made by application of the method of imparting insect-repelling properties to a base substance described above. Thus, the insect-repelling preparation of the invention includes an active ingredient as defined above and a biologically innocuous carrier, or, alternatively, a carrier having other, selected biological effects. The term "biologically innocuous carrier" shall be deemed to refer to materials that inflict no more harm to living materials than is acceptable under proposed conditions of use, as well as materials that readily evaporate or change in nature under such conditions of use to leave no residue unacceptably harmful. The carrier may be a liquid in which the active ingredient may be dissolved or, alternatively, suspended. Either solid or liquid extenders may be used. Thus, an active ingredient may be applied to sawdust or other divisible solid by an appropriate method of application, such as those discussed above. Solid extenders shall also be deemed to include paraffin-based materials and comparable materials that may be formed into blocks.

The following examples are presented to illustrate the invention and to facilitate a clearer understanding of the invention. It should be understood, however, that while the examples indicate preferred embodiments, they are not intended to limit the invention in any way. There are changes and modifications within the spirit and scope of the invention which will become apparent to those skilled in the art from this detailed description.

EXAMPLES

Experiment 1

Demonstration of Insect-Repelling Properties of Butyl Palmitate and Methyl Myristate Experiment 1 was designed to test the effectiveness of butyl palmitate (TCI American Organic Chemicals, American Tokyo KASE1, Portland, Ore.) and methyl myristate (Aldrich Co., Milwaukee, Wis.) as repellents against honey bees. For this experiment, two sugar water feeders were placed one-to-two meters from a honey bee hive outlet. The sugar water feeders were prepared as follows. A 40% sugar solution was made and placed in two inverted jar feeders set on black plexiglass plates on ringstands. Three substances were tested: butyl palmitate, lecithin, and methyl myristate. Butyl palmitate has been found to be the active component found in Ropalidia defensive secretions. Methyl myristate is an analog of methyl palmitate, the active component on Polistes defensive secretions. Lecithin was tested only because it is the main ingredient of Pam ®, a brand of non-stick cooking spray. According to conventional wisdom, Pam ® is suspected of repelling honey bees.

For each test, a coating of the substance was smeared over the entire surface of the plexiglass base and the edge of the plexi-disk forming the base of the feeder. The apparatus was then placed in front of the hive entrance. The number of bees making contact with each feeder was recorded every two minutes.

After each substance was tested, a control was tested to help insure that the previous material had been removed prior to the next test. The control was basically the same apparatus after it had been washed and rinsed well. The control contained no alleged insect-repelling substance. The control feeder was not disturbed during the entire run of tests.

Most bees tended to land on the vertical edge of the plexiglass disk forming the bottom of each feeding jar. This was a coated surface. Smaller numbers would land on the side of the jar above the meniscus of sugar water, facing down to reach it. Fewer still tended to land on the plexiglass base and walk to the plexiglass disk.

The results of this experiment are illustrated in Table 1 as follows:

TABLE 1

| Time (hrs) | Downwind Feeder | Upwind Feeder |
|---|---|---|
| 1435-1440 | Butyl palmitate: 3 | Control: 86 |
| 1450-1452 | Cleaned: 22 | Control: 35 |
| 1506-1508 | Lecithin: 4 | Control: 36 |
| 1518-1520 | Cleaned: 16 | Control: 28 |
| 1535-1537 | Methyl myristate: 9 | Control: 42 |

Judging from the results, butyl palmitate appeared to have the highest insect-repelling characteristics. Many bees hovered above and downward of the treated feeder but would not land.

Experiment 2

Demonstration of Yellow Jacket-Repelling Characteristics of Methyl Myristate, Methyl Palmitate and Butyl Palmitate In this experiment, German yellow jackets (*Vespula germanica*) were subjected to full, opened soda cans containing RC Cola® whose tops had been lightly coated with methyl myristate, methyl palmitate (Eastman Kodak Co., Rochester, N.Y.) and butyl palmitate for two days. Additionally, some opened soda cans were used as a control. The soda cans were placed in the open and recorded every 15 minutes to determine the number of yellow jackets that landed on each of them. Tests were conducted on Sep. 26-29, 1989 in Cross Plains, Wis. The temperature varied between 11°-15° C. throughout this study.

The results of this experiment are illustrated in Table 2 as follows:

TABLE 2

| Component | No. Insects Not Repelled | No. Insects Repelled | Total Contacts With Soda Can |
|---|---|---|---|
| Methyl Myristate | 19 | 14 | 33 |
| Methyl Palmitate | 70 | 4 | 74 |
| Butyl Palmitate | 3 | 23 | 26 |
| Control | 46 | 3 | 49 |

The results indicate that methyl myristate and butyl palmitate successfully repelled yellow jackets. Butyl palmitate appeared to have the highest repellency characteristics. Additionally, the repellency of the soda can with the butyl palmitate surface lasted approximately three days. Although methyl palmitate had only limited success in repelling yellow jackets, prior studies by the inventors have shown methyl palmitate to be effective. The results of this study are believed to be due to cold weather which causes the methyl palmitate to solidify thus diminishing its repelling qualities.

Experiment 3

Demonstration of Effectiveness of Methyl Palmitate and Methyl Myristate as a Repellent Against the Common House Fly (*Musca domestica*)

A 500 ml erlenmeyer flask containing a 50:50 mixture of honey and water was inverted onto a small petri dish such that only a small of amount of "honeywater" along the dish's rim was available to flies. The food container was placed 0.75 m from the ground on a chemistry rind stand, and a 20 cm by 30 cm glass plate was placed directly under the petri dish. Flies invariably walked across the glass plate to get to the food source.

Each treatment consisted of 8 ml of a solution poured onto the center of the plate, forming a thin, dry film, having a 5 cm radius around the petri dish. The number of flies that flew away upon contact with the chemical surface (repelled) and the number that continued toward the food source (not repelled) were recorded for five minutes. Six trials were conducted, each consisting of three treatments; methyl myristate (MM), methyl palmitate (MP) and a control (clean plate), presented in random order.

Mixtures were 1.0 g methyl myristate /100 ml hexane, and 1.0 g methyl palmitate /100 ml hexane. Tests were conducted 8-14 Aug. 1988 on a farm in Cross Plains, Wis., a location with a high density of house flies. Temperature was approximately 30° C. throughout this study.

A chi-square contingency table was constructed from the pooled data of the six trials to determine if there were any significant differences in the repellency of MM, MP and the control to the flies.

The results of this experiment are illustrated in Table 3 as follows:

TABLE 3

| Component | No. Insects Not Repelled | No. Insects Repelled | Total Contacts |
|---|---|---|---|
| Methyl Myristate | 4 | 47 | 51 |
| Methyl Palmitate | 4 | 56 | 60 |
| Control | 70 | 2 | 72 |

There was no significant difference between the repellency of methyl myristate or methyl palmitate (chi-square=0.048, p>0.25) to *M. domestica* adults. This data was pooled for comparison against the control. *M. domestica* adults were repelled significantly more frequently by the treatments than by the control (chi-square=144; p<0.001).

Experiment 4

Demonstration of Effectiveness of Methyl Myristate as a Repellent Against a Species of Parasitic Fly (*Sarcophaga bullata*)

In each laboratory trial four petri dishes, each with 50 g putrid ground beef mixed with either 0 ml, 0.25 ml, 0.5 ml, or 1 ml of undiluted MM, were exposed to a colony of *S. bullata*. In each of five blocks the four dishes (treatments) were arranged at random around the center of a Bioquip screen cage (0.6 m on a side) containing >300 adults *S. bullata*. A 150 W flood bulb was placed 2 cm above the center of the cage. Room temperature ranged from 22°-24° C.

The number of adult flies on each dish was recorded every 15 minutes for 1.5 hours and the mean number per dish was calculated for each block. The number of larvae (*S. bullata* larviposits) in each dish was counted after 48 hours. The means number of adults, and the number of larvae from each dish were compared using a two-factor ANOVA (treatments and blocks). The degree of methyl myristate repellency for each treatment was expressed by the percentage ratio method (Laake E. W., at al., 1931, "The Chemotropic Response of the House Fly, the Green Bottle Flies and the Black Blowfly," *U.S.D.A. Tech. Bull. No. 270.*, 11p.)

The results of this experiment are illustrated in Tables 4 and 5 as follows:

TABLE 4

| Two-Factor ANOVA on the Repellency of Methyl Myristate to *S. bullata** | | | | |
|---|---|---|---|---|
| Source | Sum of Squares | Mean Square | F | P |
| treatments | 3 | 716.19 | 238.73 | 4.64 | <0.05 |
| blocks | 4 | 680.90 | 170.22 | 3.31 | <0.05 |
| error | 12 | 619.91 | 51.40 | | |
| total | 19 | | | | |

*Tests were blocked on the separation in time for each trial.

TABLE 5

Number of *S. bullata* Landing on Methyl Myristate Treated Baits Compared with the Number Landing on Untreated Bait[a]

| Treatment | No. Dishes | No. Landed | % Ratio |
|---|---|---|---|
| control (untreated) | 5 | 567 | *[b] |
| 0.25 ml MM | 5 | 243 | 42.8 |
| 0.5 ml MM | 5 | 247 | 43.6 |
| 1.0 ml MM | 5 | 22 | 3.8 |

[a] The results are expressed as the percentage ratio or coefficient of efficacy (Laake et al., 1931, supra). A percentage ratio of 0 indicates perfect repellent action, a ratio of 100, no repellent effect.
[b] Percentage ratio is determined by dividing the total number of flies in treated dish by the number in the check dish and multiplying by 100.

A significant difference in repellency of methyl myristate to *S. bullata* was found between treatments and between blocks (Table 4). The block effect may be the result of changes in the physiological age (and thus readiness to larviposit) of the flies between experiments. Only the 1.0 ml treatment was significantly different than the 0 ml treatment (Tukey's procedure, [alpha]=0.05). Using the percentage ratio method, the 1.0 ml treatment had a rating of 3.8, indicating strong repellency (Table 5).

Although the methods and preparations disclosed above are those preferred in the practice of the invention, it will be apparent that other steps and other materials are possible. It is understood that the present invention is not limited to the particular, preferred embodiment disclosed above. Instead, it embraces all such modified forms thereof as come within the scope of the following claims.

We claim:

1. A non-insecticidal method for repelling social-stinging insects from a surface comprising applying an effective repelling quantity of a social-stinging insect repelling substance selected from the group consisting of methyl myristate, methyl palmitate, butyl palmitate and a combination thereof to the surface.

2. The method of claim 1 including the steps of:
   (a) applying to the surface the social-stinging insect repelling substance consisting essentially of an active ingredient dissolved in a selected liquid carrier, the active ingredient selected from the group consisting of methyl myristate, methyl palmitate, butyl palmitate, and a combination thereof, and
   (b) drying the liquid carrier to leave on the surface a deposit of the active ingredient.

3. The method of claim 2 wherein the liquid carrier is a nonpolar solvent.

4. The method of claim 3 wherein the insect repelling substance is further applied to a solid extender capable of adsorbing the insect repelling substance and the liquid carrier.

5. The method of claim 1 wherein the insect repelling substance is applied to an ointment-based carrier capable to adsorbing the insect repelling substance.

6. The method of claim 1 wherein the insect repelling substance is butyl palmitate.

7. A non-insecticidal method for repelling yellow jackets from a surface surrounded with yellow jackets comprising applying an effective non-insecticidal repelling quantity of a yellow-jacket repelling substance selected from the group consisting of methyl myristate, methyl palmitate, butyl palmitate, and a combination thereof, and a non-interfering carrier.

8. The method of claim 7 wherein the non-interfering carrier is selected from the group consisting of a liquid non-polar solvent carrier, a solid carrier, and an ointment-based carrier.

9. A method for protecting animals and humans against social-stinging insects which comprises applying to the skin of such animal or human a social-stinging non-insecticidal insect repelling effective amount of butyl palmitate in a non-interfering carrier.

10. The method of claim 1 wherein the social-stinging insects are selected from the group consisting of yellow jackets, wasps and bees.

* * * * *